(12) United States Patent
Gilar et al.

(10) Patent No.: US 8,123,949 B2
(45) Date of Patent: Feb. 28, 2012

(54) METHODS FOR SEPARATING COMPOUNDS

(75) Inventors: Martin Gilar, Franklin, MA (US); Uwe D. Neue, Ashland, MA (US)

(73) Assignee: Waters Technologies Corporation, Milford, MA (US)

( * ) Notice: Subject to any disclaimer, the term of this patent is extended or adjusted under 35 U.S.C. 154(b) by 990 days.

(21) Appl. No.: 11/795,650

(22) PCT Filed: Jan. 20, 2006

(86) PCT No.: PCT/US2006/001968
§ 371 (c)(1),
(2), (4) Date: Mar. 14, 2008

(87) PCT Pub. No.: WO2006/078859
PCT Pub. Date: Jul. 27, 2006

(65) Prior Publication Data
US 2009/0126466 A1   May 21, 2009

Related U.S. Application Data

(60) Provisional application No. 60/686,268, filed on May 31, 2005, provisional application No. 60/655,840, filed on Feb. 23, 2005, provisional application No. 60/645,810, filed on Jan. 20, 2005.

(51) Int. Cl.
*B01D 15/08* (2006.01)
(52) U.S. Cl. .................................. 210/656; 210/198.2
(58) Field of Classification Search .................. 210/635, 210/656, 659, 198.2; 422/70; 436/161
See application file for complete search history.

(56) References Cited

U.S. PATENT DOCUMENTS
5,398,539 A    3/1995   Gordon et al.
(Continued)

FOREIGN PATENT DOCUMENTS
EP        06718965.4        2/2010
(Continued)

OTHER PUBLICATIONS

Wagner, K. et al. "An Automated On-Line Multidimensional HPLC System for Protein and Peptide Mapping with Integrated Samle Preparation" Analytical Chemistry,74(4): 809-820 (2002).

(Continued)

*Primary Examiner* — Ernest G Therkorn
(74) *Attorney, Agent, or Firm* — Edwards Wildman Palmer LLP; Peter C. Lauro, Esq.; Mark D. Russett

(57) ABSTRACT

Methods and systems for analyzing samples using multi-dimensional chromatography are disclosed.

42 Claims, 4 Drawing Sheets

U.S. PATENT DOCUMENTS

| | | | |
|---|---|---|---|
| 6,730,228 B2 | 5/2004 | Petro et al. | |
| 6,802,967 B2* | 10/2004 | Masuda et al. | 210/198.2 |
| 7,176,298 B2* | 2/2007 | Tchaga et al. | 536/23.4 |
| 2004/0033591 A1 | 2/2004 | Lubman et al. | |
| 2004/0180415 A1* | 9/2004 | Tchaga et al. | 435/183 |
| 2009/0023898 A1* | 1/2009 | Tchaga et al. | 530/344 |
| 2010/0300971 A1* | 12/2010 | Jiang et al. | 210/656 |

FOREIGN PATENT DOCUMENTS

| | | |
|---|---|---|
| JP | 2003149218 | 5/2003 |
| JP | 20008537994 | 10/2008 |

OTHER PUBLICATIONS

Venkatramani C.J. et al. "An Automated Orthogonal Two-Dimensional Liquid Chromatograph" Analytical Chemistry 75 (14): 3484-3494 (2003).

Strege, M.A. "Mixed-Mode Anion-Cation Exchange/Hydrophilic Interaction Liquid Chromatography-Elecrospray Mass Spectrometry as an Alternative to Reversed Phase for Small Molecule Drug Discovery" Analytical Chemistry 72(19): 4629-4633 (2000).

Sionecker, P.J. "Informational Orthogonality of Two-Dimentional Chromatographic Separations" Analytical Chemistry 64(4): 682-689 (1996).

PCT/ISA/210, Abbott GMBH & Co. KG, International Search Report for PCT/EP2006/007839.

H. Toll et al., "Operational Variables for Fast Peptide Analysis Using Monolithic Columns", Poster, presented at the 28th International Symposium on High Performance Liquid Phase Separations, Jun. 12-13, 2004, Philadelphia, PA (HPLC 2004).

Tranchida, PQ, et al., J. Chromotagr. A. 1054 (1-2): 3-16 (2004).

H. Toll et al., "Separation, Detection, and Identification of Peptides by Ion-Pair Reversed-Phase High-Performance Liquid Chromatography-Electrospray Ionization Mass Spectrometry at High and Low pH", J. Chromatogr. A 1079: 274-286 (2005).

PCT/ISA/237, Abbott GMBH & Co. KG, Writen Opinion for PCT/EP2006/007839.

Washburn, M.P. et al., 3rd Nat. Biotechnol. 2001, 19, 242-247.

Wagner, K., et al; Anal. Chem. 2002, 74, 809-820.

Peng, J. et al., J Proteome Res 2003, 2, 43-50.

Kachman, M.T., et al.; Anal. Chem. 2002, 74, 1779-1791.

Silva, J.C., et al; Anal. chem. 2005, in print.

Tolley, L., et al; Anal. Chem. 2001, 73, 2985-2991.

Shen, Y., et al; Anal. Chem. 2004, 76, 1134-1144.

Wehr, T.; LCGC North America 2002, 20, 954-962.

Stadalius, M.A., et al; J. Chromatogr. 1987, 387, 21-40.

Ghrist, B.F., et al; J. Chromatogr. 1987, 387, 1-19.

Neue, U.D., et al; Design of rapid gradient methods for the analysis of combinatorial chemistry libraries and the preparation of pure compound; Marcel Dekker: New York, 2001.

Gilar, M., et al; J. Chromatogr, A 2004, 1061, 183-192.

Giddings, J.C.; J. High. Res. Chromatogr. 1987, 10, 319-323.

Liu, Z., et al; Anal. Chem. 1995, 67, 3840-3845.

Slonecker, P.J., et al; Anal. Chem. 1996, 68, 682-689.

Giddings, J.C.; J. Chromatogr, A 1995, 703, 3-15.

Gilar, M, et al; J. Sep. Sci. 2005, 28, 1694-1703.

Gray, M., et al; J. Chromatogr. A 2002, 975, 285-297.

Gygi, S.P., et al; Nat. Biotechnol. 1999, 17, 994-999.

Chloupek, R.C., et al; J. Chromatogr. A 1994, 686, 45-59.

Hancock, W.S., et al; J. Chromatogr. A 1994, 686, 31-43.

Guo, D.C., et al; J. Chromatogr. 1987, 386, 205-222.

Toll, H., et al; J. Chromatogr. A 2005, pp. 274-286.

Opiteck, G.J., et al; 3rd Anal. Chem. 1997, 69, 2283-2291.

Alpert, A.J.; J. Chromatogr. 1990, 499, 177-196.

Yoshida, T.; Anal. Chem. 1997, 69, 3038-3043.

Zhu, B.Y., et al; J. Chromatogr. 1991, 548, 13-24.

Vollmer, M., et al; Anal. Chem. 2004, 76, 5180-5185.

Alpert, A.J., et al; J. Chromatogr. 1988, 443, 85-96.

Davis, J. M.; J. Sep. Sci. 2005, 28, 347-359.

Murphy, R.E., et al; Anal. Chem. 1998, 70, 1585-1594.

Wolters, D.A., et al; Anal. Chem. 2001, 73, 5683-5690.

Naidong, W., et al; Biomed. Chromatogr. 2004, 18, 28-36.

Man, P., et al; Proteomics 2005, 5, 113-122.

Gilar, M., et al; Anal. Chem. (2005) 77, 6426-6434.

Maynard, D.M., et al. "Charaterizing Complex Peptide Mixtures Using a Multi-Dimensional Liquid Chromatography-Mass Spectrometry System: Saccharomyces Cerevisiae as a Model System" Journal of Chromatography B 810 (2004) 69-76.

* cited by examiner

US 8,123,949 B2

METHODS FOR SEPARATING COMPOUNDS

CROSS-REFERENCE TO RELATED APPLICATIONS

This application is the U.S. national phase application, pursuant to 35 U.S.C. §371, of PCT international application Ser. No. PCT/US06/001968, filed Jan. 20, 2006, designating the United States and published in English on Jul. 27, 2006 as publication WO 2006/078859 A2, which claims priority to U.S. provisional application Ser. Nos. 60/645,810, filed Jan. 20, 2005, 60/655,840, filed Feb. 23, 2005, and 60/686,268, filed May 31, 2005. The entire contents of the aforementioned patent applications are incorporated herein by this reference.

BACKGROUND OF THE INVENTION

Chemical and biological samples often contain mixtures of compounds. A variety of chromatographic techniques for separation of mixtures have been developed, and many systems for chromatographic separation and purification are commercially available.

Among the best-known chromatographic techniques are gas chromatography, high performance liquid chromatography (HPLC) and super-critical fluid chromatography (SFC). HPLC methods can be used to separate polar and non-polar compounds; the solvent (or mobile phase) and stationary phase to be used in an HPLC method are chosen based upon the types of analytes to be separated. With careful selection of the mobile phase and stationary phase, many mixtures can be separated into well-resolved peaks or fractions which can be isolated for further analysis or use. Characterization by methods such as mass spectrometry (MS) provides information about the analytes present in the sample.

A variety of HPLC techniques have been reported. Among the most widely-used are "normal phase" HPLC (generally useful for relatively polar analytes; least-polar analytes usually elute first) and "reversed phase" HPLC (RP-HPLC, generally used for less polar analytes; least-polar analytes generally elute last). A variation known as "hydrophilic interaction chromatography" or HILIC is useful for highly polar analytes that would not be sufficiently retained on a reversed-phase column.

However, when complex mixtures are involved, a single chromatographic (e.g., HPLC) separation may not be capable of separating all of the compounds into well-separated peaks or fractions. If peaks are not well-resolved, impurities or contaminants may be present even after separation, interfering with characterization of a collected fraction. To address this problem, multi-dimension chromatographic methods have been developed. In these methods, a sample is subjected to a first separation. The solvent stream resulting from the first separation is typically collected in fractions representing partially-purified compound mixtures; individual fractions are then selected and subjected to a second separation technique. The conditions of the first and second separations are generally different, and, if chosen carefully, the second separation should permit the separation of compounds which were not resolved in the first separation dimension. Examples of such multi-dimensional chromatographic methods include, e.g., Tranchida, P Q et al. *J. Chromatogr A.* 1054(1-2):3-16 (2004).

Such methods often involve the use of different columns and different mobile phases in each of the two chromatographic methods, which can result in added complexity. For example strong-cation exchange (SCX) separation followed by RP-HPLC has been used to analyze peptide mixtures. However, the high salt concentrations and/or organic solvents often required by the SCX conditions may not be compatible with the conditions required for RP-HPLC, and additional sample work-up is often required.

Furthermore, the mobile phases or mobile phase additives used in the two separations may not be compatible with detectors, including mass spectrometers, or other parts of the analytical system, leading to additional difficulty in detection or sample processing.

SUMMARY OF THE INVENTION

It has now been found that multi-dimensional HPLC can be performed using an HPLC separation for both the first and second dimensions by varying the pH of the mobile phase used in the two separations.

In one embodiment, the invention provides a method for analyzing a sample containing at least one analyte, the method including the steps of: a) subjecting the sample to a first liquid chromatographic separation mode at a first pH with a first mobile phase; b) collecting (or sampling) at least one fraction (or portion) from the first chromatographic separation; c) subjecting the at least one fraction to a second liquid chromatographic separation mode at a second pH with a second mobile phase; and (optionally) d) detecting the presence or absence of the at least one analyte in the sample; wherein the first pH and the second pH are different.

In certain preferred embodiments, first and second chromatographic separations are substantially orthogonal to each other. In certain preferred embodiments, the first chromatographic separation mode is high performance liquid chromatography (HPLC), preferably HILIC or RP-HPLC. In certain preferred embodiments, the second chromatographic separation mode is high performance liquid chromatography (HPLC), preferably HILIC or RP-HPLC. In certain preferred embodiments, the first and/or second chromatographic separation has a peak capacity of at least 100 peaks.

In certain preferred embodiments, the first pH and the second pH differ by at least about 3 pH units. In certain preferred embodiments, method of claim 1, wherein the at least one analyte is a peptide, polypeptide, or protein. In certain preferred embodiments, the at least one analyte is a small organic molecule. In certain preferred embodiments, the sample contains at least 10 analytes. In certain preferred embodiments, the sample contains at least 100 analytes. In certain preferred embodiments, the sample contains at least 1000 analytes. In certain preferred embodiments, the total peak capacity of the method is at least 1,000, 5,000, or 10,000 peaks. In certain preferred embodiments, the first and/or second chromatographic separation is performed using a microbore column, capillary column, or nanocolumn.

In certain preferred embodiments, the at least one fraction or portion collected or sampled in step b) is concentrated or diluted prior to subjecting the at least one fraction to the second chromatographic separation mode; in certain embodiments, the at least one fraction is concentrated by evaporation. In other preferred embodiments, the at least one fraction (or portion) collected (or selected) in step b) is diluted on-line prior to performing the second chromatographic separation mode. In certain embodiments, the at least one fraction collected in step b) is diluted using on-line dilution.

In certain preferred embodiments, the step of detecting is performed using a mass spectrometer. In certain preferred embodiments, the first and second chromatographic modes are the same. In certain preferred embodiments, the first and/or second mobile phase is substantially free of non-volatile salts. In certain preferred embodiments, the second mobile phase comprises less than about 20 mM (more preferably less than 10 or 5 mM) non-volatile salts. In certain preferred embodiments, the first and/or second mobile phase contains less than about 20 mM of volatile salts.

In another embodiment, the invention provides a method for separating a plurality of analytes in a sample. The method includes the steps of a) subjecting at least a portion of the sample to a first chromatographic separation mode at a first pH; b) collecting (or selecting) at least one fraction (or portion) from the first chromatographic separation; and c) subjecting the at least one fraction to a second chromatographic separation mode at a second pH; under conditions such that at least two analytes in the sample are separated.

In certain preferred embodiments, first and second chromatographic separations are substantially orthogonal to each other. In certain preferred embodiments, the first chromatographic separation mode is high performance liquid chromatography (HPLC), preferably HILIC or RP-HPLC. In certain preferred embodiments, the second chromatographic separation mode is high performance liquid chromatography (HPLC), preferably HILIC or RP-HPLC. In certain preferred embodiments, the first and/or second chromatographic separation has a peak capacity of at least 100 peaks.

In certain preferred embodiments, the first pH and the second pH differ by at least about 3 pH units. In certain preferred embodiments, method of claim 1, wherein the at least one analyte is a peptide, polypeptide, or protein. In certain preferred embodiments, the at least one analyte is a small organic molecule. In certain preferred embodiments, the sample contains at least 10 analytes. In certain preferred embodiments, the sample contains at least 100 analytes. In certain preferred embodiments, the sample contains at least 1000 analytes. In certain preferred embodiments, the total peak capacity of the method is at least 1,000, 5,000, or 10,000 peaks. In certain preferred embodiments, the first and/or second chromatographic separation is performed using a microbore column, capillary column, or nanocolumn.

In certain preferred embodiments, the at least one fraction or portion collected or sampled in step b) is concentrated or diluted prior to subjecting the at least one fraction to the second chromatographic separation mode; in certain embodiments, the at least one fraction is concentrated by evaporation. In other preferred embodiments, the at least one fraction (or portion) collected (or selected) in step b) is diluted on-line prior to performing the second chromatographic separation mode. In certain embodiments, the at least one fraction collected in step b) is diluted using on-line dilution.

In certain preferred embodiments, the step of detecting is performed using a mass spectrometer. In certain preferred embodiments, the first and second chromatographic modes are the same. In certain preferred embodiments, the second mobile phase is substantially free of non-volatile salts. In certain preferred embodiments, the first and/or second mobile phase comprises less than about 20 mM (more preferably less than 10 or 5 mM) non-volatile salts. In certain preferred embodiments, the first and/or second mobile phase contains less than about 20 mM of volatile salts.

In another embodiment, the invention provides a method for characterizing a sample containing a plurality of polypeptides in a two-dimensional (or multi-dimensional) liquid chromatography system. The method includes the steps of: a) injecting the sample into a first dimension chromatography apparatus of said two-dimensional (or multi-dimensional) liquid chromatography system; b) chromatographically separating at least a first polypeptide component of said sample from at least a second polypeptide of said sample in a chromatography column of said first dimension chromatography apparatus using a first mobile phase; c) eluting said separated first and second polypeptide components in an eluent from said chromatography column; d) sampling at least one discrete volume of said eluent; e) injecting said at least one discrete volume into a second dimension chromatography apparatus of said two-dimensional (or multi-dimensional) liquid chromatography system; f) subjecting the injected discrete volume to a chromatographic separation in a chromatography column of said second dimension chromatography apparatus using a second mobile phase, wherein the pH of said first and second mobile phases differs by about 3 pH units; (optionally) g) characterizing an eluent from said chromatography column of said second dimension chromatography apparatus using mass spectroscopy, thereby characterizing the sample containing a plurality of polypeptides.

In certain preferred embodiments, first and second chromatographic separations are substantially orthogonal to each other. In certain preferred embodiments, the first chromatographic separation mode is high performance liquid chromatography (HPLC), preferably HILIC or RP-HPLC. In certain preferred embodiments, the second chromatographic separation mode is high performance liquid chromatography (HPLC), preferably HILIC or RP-HPLC. In certain preferred embodiments, the first and/or second chromatographic separation has a peak capacity of at least 100 peaks.

In certain preferred embodiments, the first pH and the second pH differ by at least about 3 pH units. In certain preferred embodiments, the at least one analyte is a small organic molecule. In certain preferred embodiments, the sample contains at least 10 analytes. In certain preferred embodiments, the sample contains at least 100 analytes. In certain preferred embodiments, the sample contains at least 1000 analytes. In certain preferred embodiments, the total peak capacity of the method is at least 1,000, 5,000, or 10,000 peaks. In certain preferred embodiments, the first and/or second chromatographic separation is performed using a microbore column, capillary column, or nanocolumn.

In certain preferred embodiments, the at least one fraction or portion collected or sampled in step b) is concentrated or diluted prior to subjecting the at least one fraction to the second chromatographic separation mode; in certain embodiments, the at least one fraction is concentrated by evaporation. In other preferred embodiments, the at least one fraction (or portion) collected (or selected) in step b) is diluted on-line prior to performing the second chromatographic separation mode. In certain embodiments, the at least one fraction collected in step b) is diluted using on-line dilution.

In certain preferred embodiments, the step of detecting is performed using a mass spectrometer. In certain preferred embodiments, the first and second chromatographic modes are the same. In certain preferred embodiments, the second mobile phase is substantially free of non-volatile salts. In certain preferred embodiments, the first and/or second mobile phase comprises less than about 20 mM (more preferably less than 10 or 5 mM) non-volatile salts. In certain preferred embodiments, the first and/or second mobile phase contains less than about 20 mM of volatile salts.

In another embodiment, the invention provides a method for purifying a compound in a sample containing the compound and at least two impurities. The method includes the steps of a) subjecting the sample to a first chromatographic separation mode at a first pH, under conditions such that the compound is separated from a first impurity; b) collecting at least one compound-containing fraction from the first chromatographic separation; c) subjecting the at least one compound-containing fraction to a second chromatographic separation mode at a second pH, under conditions such that the compound is separated from a second impurity; and d) collecting the purified compound.

In certain preferred embodiments of any of the methods described herein, the method can further include the step of identifying one, some, or all of the compound(s) and/or impurities present in the sample. In certain preferred embodiments, the identification is performed by mass spectrometry.

In another embodiment, the invention provides a liquid chromatography system for separating a mixture of compounds. The system includes: a) a first chromatographic analysis system comprising a first chromatographic column and a pump for pumping a first mobile phase through the first chromatographic column; b) a second chromatographic analysis system comprising a second chromatographic column and a pump for pumping a second mobile phase through the second chromatographic column; c) means for selecting at least one compound-containing fraction from an effluent stream of the first chromatographic column and introducing the at least one compound-containing fraction into the second chromatographic column; wherein the pH of the first mobile phase and the pH of the second mobile phase are different.

In certain preferred embodiments, the system further comprises a detector, more preferably a mass spectrometer. In certain preferred embodiments, the first and second chromatographic modes are the same. In certain preferred embodiments, the second mobile phase is substantially free of non-volatile salts. In certain preferred embodiments, the first and/or second mobile phase comprises less than about 20 mM (more preferably less than 10 or 5 mM) non-volatile salts. In certain preferred embodiments, the first and/or second mobile phase contains less than about 20 mM of volatile salts.

DETAILED DESCRIPTION OF THE INVENTION

Figure 1:
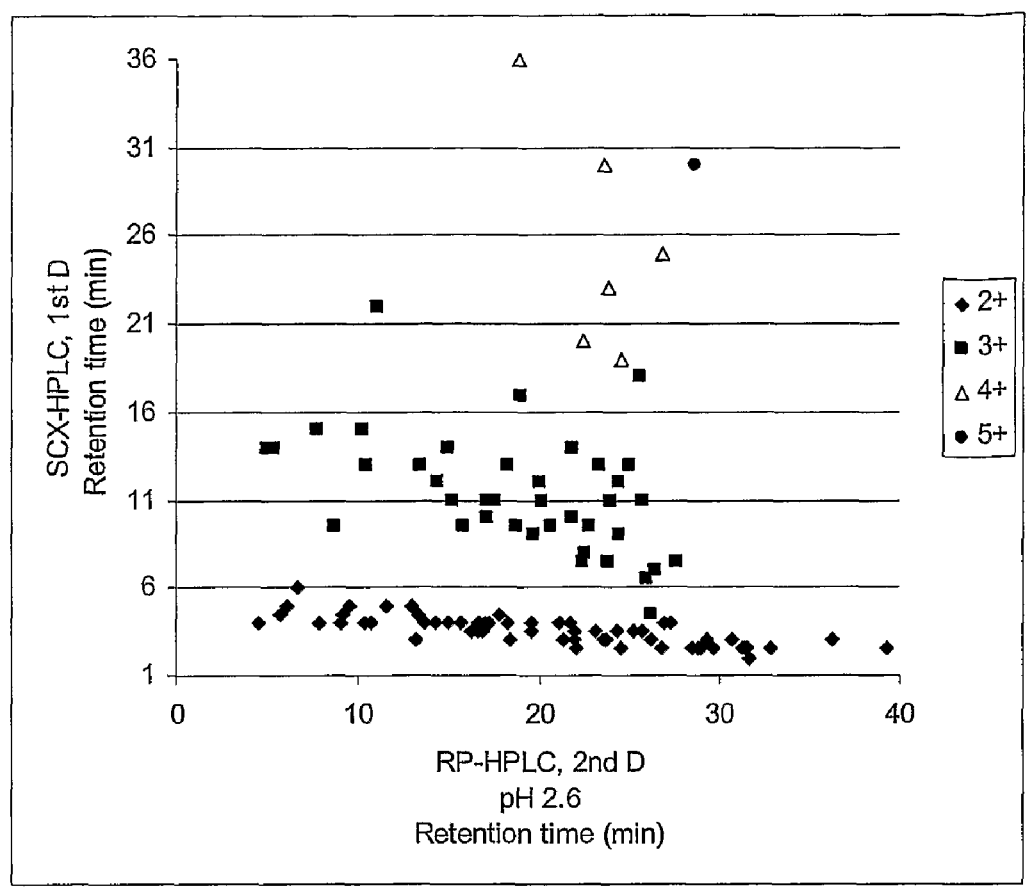
FIG. 1 is a plot showing the separation resulting from a multi-dimensional LC separation system using SCX in the first dimension and RP-HPLC in the second dimension.

The present invention provides methods and systems for separating, purifying, and/or analyzing a compound or mixture of compounds. The methods and systems of the invention are capable of separating and thereby resolving complex mixtures of compounds, allowing rapid identification of components of such mixtures.

The compounds present in the mixture can be, e.g., small organic molecules (such as pharmaceuticals or candidate pharmaceuticals), peptides or polypeptides (e.g., from peptide synthesis or from biological samples, including digests of proteins or mixtures of proteins), nucleic acids or polynucleotides (e.g., from biological samples or from synthesized polynucleotides), synthetic or natural polymers, or mixtures of these materials. The types of compounds are limited only by the chromatographic methods selected for compound separation, as described herein. In preferred embodiments, at least one compound or impurity is at least partially charged at a pH in the range of about 2 to about 12. More preferably, at least one compound or impurity has a first charge state at a first pH in the range of about 2 to about 12 and a second charge state at a second pH in the range of about 2 to about 12. For example, a compound could have a charge of +1 at a lower pH, and have a charge of 0 (neutral) at a higher pH; or a charge of +2 at a lower pH, a charge of +1 at a higher pH, and a charge of 0 at a third, still higher pH. In certain preferred embodiments, an analyte to be detected, analyzed, or purified is a peptide, polypeptide, or protein.

Thus, in one aspect, the invention provides methods for analyzing a sample containing at least one analyte. The methods generally include the steps of a) subjecting the sample to a first chromatographic separation mode at a first pH with a first mobile phase; b) collecting or selecting at least one fraction from the first chromatographic separation; c) subjecting the at least one fraction to a second chromatographic separation mode at a second pH with a second mobile phase; and (optionally) d) detecting the presence or absence of the at least one analyte in the sample; wherein the first pH and the second pH are different.

In another aspect, the invention provides a method for separating a plurality of analytes in a sample. The method includes the steps of a) subjecting at least a portion of the sample to a first chromatographic separation mode at a first pH; b) collecting at least one fraction from the first chromatographic separation; and c) subjecting the at least one fraction to a second chromatographic separation mode at a second pH; under conditions such that at least two analytes in the sample are separated.

In another embodiment, the invention provides a method for characterizing a sample containing a plurality of polypeptides in a two-dimensional liquid chromatography system. The method includes the steps of a) injecting the sample into a first dimension chromatography apparatus of said two-dimensional liquid chromatography system; b) chromatographically separating at least a first polypeptide component of said sample from at least a second polypeptide of said sample in a chromatography column of said first dimension chromatography apparatus using a first mobile phase; c) eluting said separated first and second polypeptide components in an eluent from said chromatography column; d) sampling at least one discrete volume of said eluent; e) injecting said at least one discrete volume into a second dimension chromatography apparatus of said two-dimensional liquid chromatography system; f) subjecting the injected discrete volume to a chromatographic separation in a chromatography column of said second dimension chromatography apparatus using a second mobile phase, wherein the pH of said first and second mobile phases differs by about 3 pH units; and g) characterizing an eluent from said chromatography column of said second dimension chromatography apparatus using mass spectroscopy, thereby characterizing the sample containing a plurality of polypeptides.

In still another aspect, the invention provides a method for purifying a compound in a sample containing the compound and at least two impurities. The method includes the steps of a) subjecting the sample to a first chromatographic separation mode at a first pH, under conditions such that the compound is separated from a first impurity; b) collecting at least one compound-containing fraction from the first chromatographic separation; c) subjecting the at least one compound-containing fraction to a second chromatographic separation mode at a second pH, under conditions such that the compound is separated from a second impurity; and d) collecting the purified compound.

In preferred embodiments of the methods of the invention, the pH of the first chromatographic separation mode mobile phase and the pH of the second chromatographic separation mode mobile phase are kept substantially constant during each of the first and second chromatographic separations, respectively, e.g., the separations are isocratic with respect to pH. This result can be achieved in several ways, e.g., use of a single mobile phase for the separation mode; or use of two mobile phase components which are mixed by a pump and mixing valve, each mobile phase component having similar or identical pH, so that the mobile phase applied to the column has substantially the same pH throughout the separation (see, e.g., the Examples herein); or use of two mobile phase components having similar pH and a third mobile phase component or modifier mixed in by pump in a constant amount, to provide a substantially constant mobile phase pH to the column. However, in certain embodiments, the pH of the mobile phase supplied to the first and/or second chromatographic mode can be varied over a pH range during the first and/or second chromatographic separations. In such embodiments, the pH range of the first chromatographic mode preferably differs from the pH range of the second chromatographic mode.

In preferred embodiments, the difference between the pH of the first chromatographic separation mode mobile phase and the pH of the second chromatographic separation mode mobile phase is at least 3 pH units; e.g., if the pH of the first chromatographic separation mode mobile phase is 2.5, then the pH of the second chromatographic separation mode mobile phase can be at least 5.5. In certain embodiments, the pH difference is at least about 4 pH units, 5 pH units or 6 pH units. The pH of one chromatographic separation mode mobile phase can be, e.g., between 2 and 5, while the pH of another chromatographic separation mode mobile phase can be, e.g., at least 3 pH units greater, e.g., between 5 and 8, or 5 and 10, or 7 and 12. In certain preferred embodiments, the pH of the first chromatographic mode is between about 2 and about 6, more preferably between about 2 and about 5, or between about 2.5 and about 4.5. In certain preferred embodiments, the pH of the first chromatographic mode is between about 6 and about 12, more preferably between about 6 and about 10, or between about 7 and about 10.

The chromatographic methods suitable for use in one or both of the dimensions of the invention include liquid chromatographic (including HPLC) methods such as normal-phase HPLC, RP-HPLC, HILIC, and size-exclusion chromatography (SEC), including gel permeation chromatography (GPC). Other suitable methods include additional HPLC methods and related liquid chromatographic techniques, including, e.g., ultra-performance liquid chromatography (UPLC), fast performance liquid chromatography (FPLC) and the like.

In certain embodiments, preferred separation modes are those in which the mobile phase is compatible with analytical techniques such as mass spectrometry, e.g., the mobile phase is suitable for injection into a mass spectrometer with little or no sample clean-up or desalting. Therefore, in certain preferred embodiments, the mobile phase of a separation mode in which the eluent is to be analyzed by mass spectrometry, e.g., the second chromatographic mode mobile phase, is substantially free of non-volatile salts; for example, in certain embodiments, the second mobile phase comprises less than about 20 mM (or less than 10 mM or 5 mM) of non-volatile salts. The term "non-volatile salts", as used herein, refers to salts present in the mobile phase which are substantially non-volatile under conditions used for removing mobile phase solvents when interfacing a liquid chromatography system with a mass spectrometer. This, salts such as sodium chloride or potassium phosphate are considered non-volatile salts, whereas salts such as ammonium formate, ammonium bicarbonate, or ammonium acetate, which are largely removed under vacuum, are volatile salts. Other volatile salts can be used, as will be apparent to one of ordinary skill in the art. For example, ammonium ($NH_4^+$) salts of volatile acids (e.g., formic acid, acetic acid, trifluoroacetic acid, perfluorooctanoic acid) are generally volatile salts suitable for use with MS detection.

In certain embodiments, the first or second chromatographic separation is an HPLC separation, more preferably a reversed-phase HPLC separation. In certain preferred embodiments, one or both of the first and second chromatographic separations is a HILIC separation. In certain preferred embodiments, the second chromatographic separation is of the same type as the first chromatographic separation, e.g., both the first and second chromatographic separations are RP-HPLC, or both are HILIC separations, etc.

The analytes or compounds present in the mixture can be, e.g., small organic molecules (such as pharmaceuticals or candidate pharmaceuticals, typically having a molecular weight of less than 1000), peptides or polypeptides (e.g., from peptide synthesis or from biological samples, including digests of proteins or mixtures of proteins), nucleic acids or polynucleotides (e.g., from biological samples or from synthesized polynucleotides), synthetic or natural polymers, or mixtures of these materials. The types of compounds are limited only by the chromatographic methods selected for compound separation, as described herein. In certain preferred embodiments, an analyte to be detected, analyzed, or purified is a peptide, polypeptide, or protein.

In certain embodiments, the sample to be analyzed or purified contains at least 20, 50, 100, 500, 1000, or 5000 analytes and/or compounds and/or components and/or impurities.

In order to separate the constituents of a sample mixture efficiently, separation modes having high peak capacities are preferred. For example, in certain embodiments, the first chromatographic separation mode has a peak capacity of at least 10, 20, 50, or 100 peaks, or the second chromatographic separation mode has a peak capacity of at least 10, 20, 50, or 100 peaks.

Two separations in which the retention time of a group of compounds in the first separation is not highly correlated to the retention time of the group of compounds in the second separation can be said to be "orthogonal". For example, if the retention times of a group of compounds in a first separation are plotted against the retention times of the compounds in the second separation, the correlation coefficient ($R^2$) of the resulting graph would be 1.0 if the two separations were identical, and 0.0 if the two separations were perfectly orthogonal. In certain embodiments, two separation modes are "substantially orthogonal", as that term is used herein, if the correlation coefficient ($R^2$) is less than about 0.8. In other embodiments, two separation modes are "substantially orthogonal", as that term is used herein, if orthogonality % (O %) is greater than about 30% (as determined according to the method described in Gilar, M.; Olivova, P.; Daly, A. E.; Gebler, J. C., *Anal. Chem.* (2005) 77, 6426-6434, incorporated herein by reference). In preferred embodiments, the correlation coefficient between a first separation and second separation according to the invention is less than 0.8, more preferably less than 0.6, more preferably less than 0.4, still more preferably less than 0.2, and even more preferably less than 0.1.

In two perfectly orthogonal separations, the total peak capacity of the method will be the product of the peak capacities of the individual methods (i.e., the peak capacities of the individual methods, multiplied). For example, a system in which a first separation has a peak capacity of 50 and a second, perfectly orthogonal separation has a peak capacity of 100, the total peak capacity of a system in which a compound is serially subjected to the first and second separations will be 50×100=5000 peaks. In a system in which the two separation modes are not perfectly orthogonal, the total peak capacity will be somewhat less than the product of the peak capacities of the individual methods. It will be appreciated that the peak capacity can be decreased by factors such as the frequency of fraction collection and so may be less than the theoretical peak capacity. In preferred embodiments, the method has a total peak capacity of at least 1000, 2000, 5000, or 10000 peaks.

To evaluate the orthogonality of selected LC modes (e.g., for use with peptides), peptide retention maps can be constructed, as described previously (Gilar, M.; Olivova, P.; Daly, A. E.; Gebler, J. C. *J. Sep. Sci.* (2005) 28, 1694-1703, incorporated herein by reference; see also Gilar, M.; Olivova, P.; Daly, A. E.; Gebler, J. C., *Anal. Chem.* (2005) 77, 6426-6434, incorporated herein by reference). Briefly, five protein digests (each comprising of 20-100 peptides) were sequentially injected on LC-UV-MS system, the peptides were identified by their unique mass, and their retention was recorded. Retention data were acquired for each LC mode in single-dimensional LC setup, and normalized according to equation 1.

$$RT_{i(norm)} = \frac{RT_i - RT_{min}}{RT_{max} - RT_{min}} \quad (1)$$

$RT_{max}$ and $RT_{min}$ represent the retention times of the most and least retained peptide in the data set, respectively. The retention times $RT_i$ are converted to normalized $RT_{i(norm)}$; the values of $RT_{i(norm)}$ range from 0 to 1. The normalization serves two purposes: First, it allows for comparison of different chromatographic data in a uniform 2D retention space, regardless of absolute retention time values. Second, it removes the void spaces in the 2D separation plot, where no peaks elute. The voids can be caused by column void volume, LC system gradient delay, or by using gradient spanning outside of the useful range (for example gradient of 0-100% acetonitrile in RP-LC, while practically all tryptic peptides elute within 0-50% acetonitrile).

Figure 4:
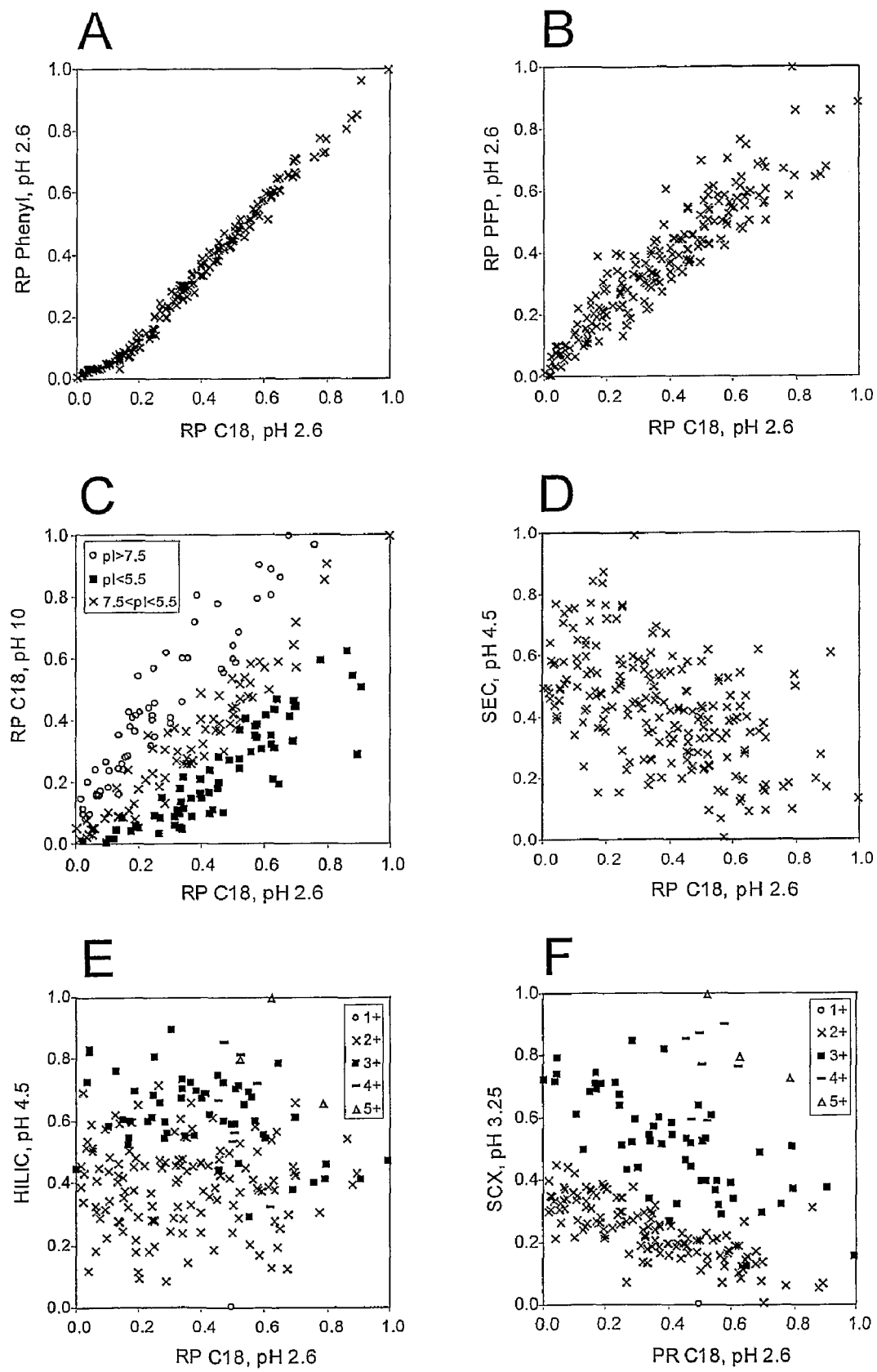
FIG. 4 shows several normalized retention time plots for selected 2D-LC systems.

The tools developed for the characterization of orthogonality in 2D-LC separation utilize several complementary descriptors, such as informational similarity, percentage of synentropy, peak spreading angle, and practical peak capacity. While those mathematical models are suitable for description for some situations, other situations (including data clusters) may be difficult to describe. Therefore, a intuitive, single descriptor can be used. The model utilizes the following approach: (i) The normalized retention data (equation 1) are plotted into a 2D separation space as shown in FIG. 4. (ii) Area is assigned to each data point, representing a normalized peak area (peak width is measured according to Snyder at 4σ, at 13.4% of peak height. (iii) The orthogonality is defined as a normalized area covered by peaks in 2D separation space. The greater is coverage, the greater the orthogonality.

Further assumptions can be made to simplify the problem: (i) 2D separation space was divided into rectangular bins, similarly as in earlier published reports. Each bin then corresponds to a peak area. (ii) The data set is superimposed with a separation space divided into the number of rectangular bins that equal the number of data points. In other words, the peak capacity of normalized 2D separation space is equal to the number of separated components. Therefore, the data sets of different sizes can be compared. (iii) The area of all normalized bins containing data point is summed. The degree of area coverage describes an orthogonality of an interrogated 2D separation system.

Columns suitable for performing separations according to the invention are known in the art and can be selected without undue experimentation. For example, RP-HPLC columns include $C_i$, $C_{18}$, and phenyl-substituted solid supports. Normal-phase columns can employ silica as the stationary phase. HILIC separations are generally performed using a silica-based column material, optionally modified with, e.g., aminopropyl or diol modifiers. Pre-packed or coated columns or capillaries are available from commercial sources; selection of a particular stationary phase or solid support for use in a separation can be made according to factors such as the amount and complexity of the mixture to separated, the type of analyte to be determined, and the like.

Similarly, the size of the column can be selected according to factors such as the amount of sample to be analyzed or purified. For analysis of larger sample quantities, an HPLC column having a diameter of about 3 mm to about 20 mm may be used. For very small amounts of sample, a microbore column, capillary column, or nanocolumn may be used.

In the methods of the invention a sample is subjected to chromatography in a first dimension (i.e., a first chromatographic mode). The sample may require clean-up, filtration, concentration, or other pre-analysis preparation prior to beginning the first chromatographic separation. The sample is then introduced into the first-dimension separation system, typically by injection through an injection valve. The components of the sample are then carried by the mobile phase of the first HPLC system into and through the first stationary phase of the multi-dimensional liquid chromatography system. At least one sample component of the sample is chromatographically separated from other sample components, such that a mobile phase eluent exiting from the first-dimension column includes two or more separated sample components. In preferred embodiments, a detector can be used to determine whether a component or components is present at any portion of the eluent stream. For example, a non-destructive detector such as a UV/VIS (ultraviolet/visible wavelength light detector) can be used to determine whether a component or analyte is present in the eluent stream. Alternatively, a small portion of the eluent stream can be split and diverted to a destructive detector such as a mass spectrometer or evaporative light-scattering detector (ELSD). A variety of such destructive and non-destructive detectors are commercially available and an appropriate detector can be selected for a particular application, depending on factors such as, e.g., the nature and amount of the expected analytes, compounds, components or impurities in the sample, the type of mobile phase being used, and the like.

Fractions or portions of eluent from the first dimension eluent stream can be selected for processing in the second dimension in several ways. For example, in certain embodiments, the information obtained from a first-dimension detector (e.g., as described above) can be used to determine which fractions or portions of the eluent stream from the first column will be directed to the second chromatographic separation. Thus, for example, the first-dimension detector can trigger a fraction collector to collect a specified fraction of eluent, or can signal a computerized chromatography analysis system to mark a specific fraction for later injection into the second dimension chromatography system. In other embodiments, fractions can be collected or sampled at pre-determined intervals or at a pre-determined frequency (e.g., a fraction is collect every 30 seconds, every minute, every two minutes, and the like) for injection into the second chromatography system. Commercially-available fraction collectors can be used in automated or manual mode to collect samples as needed.

At least a portion of the first-dimension mobile phase eluent is sampled and directed into the second HPLC dimension of the multi-dimensional chromatography system (e.g., using sample loops associated with a multi-port injection valve). The first separation mode must interface with the second separation mode to permit a fraction of the eluent from the first chromatographic separation to be introduced into the second separation mode. This interfacing can be accomplished in several ways. For example, fractions of the first-dimension eluent can be collected in a fraction collector; all or some of the fractions can be selected for introduction into the second chromatographic separation mode. If desired, the fractions can be concentrated or evaporated, e.g., to reduce volume or remove incompatible solvents prior to introduction into the second-dimension HPLC system. Other sample preparation steps, such as desalting, can also be performed on collected fractions. Alternatively, fractions or portions of eluent from the first eluent stream can be directly injected into the second-dimension separation system, e.g., by injection through a rotary multi-port injection valve (see, e.g., U.S. Pat. No. 6,730,228). In certain preferred embodiments, a fraction of the first eluent can be diluted on-line prior to performing the second chromatographic separation mode. In a preferred embodiment, the sampled portion or portions of the first-dimension eluent stream are then injected directly into the second HPLC dimension of the multi-dimensional liquid chromatography system (e.g., using a multi-port injection valve as a second-dimension injector).

At least one sample component or analyte present in the selected portions or fractions of the first dimension eluent stream is then chromatographically separated from other sample components in a second-dimension separation, such that a mobile phase eluent exiting from the second-dimension column includes two or more separated sample components. In preferred embodiments, a detector can be used to determine whether a component or components is present at any portion of the second dimension eluent stream, as described above for the first-dimension eluent stream. Mass spectrometric detection is preferred for detecting and identifying the separated components or analytes present in the sample.

The mobile phases for the first and second chromatographic separations can be selected to optimize the separation of a particular analyte or analytes, or to optimize separation of unknown components of the sample. As described elsewhere herein, the present inventors have discovered that changes in pH of the mobile phases can be used to provide at least partially orthogonal separations even when the first and second dimensions utilize the same type of separation (e.g., RP-HPLC for both dimensions, using the same type of column for each). In certain embodiments, the chromatographic columns used for the first and second dimensions can be of the same type (e.g., both reversed phase), and the mobile phases of the separations can be substantially similar, with the principal difference being a pH difference as described herein. Mobile phase pH can be altered by addition of pH modifiers to the mobile phase; for example, acids such as trifluoroacetic acid or formic acid can be added to provide lower (more acidic) pH, while ammonium hydroxide (i.e., aqueous ammonia) or other bases such as trimethylamine or triethylamine can be added to provide higher (more basic) mobile phase pH.

In another aspect, the invention provides a liquid chromatography system for separating a mixture of compounds. The system includes a) a first chromatographic analysis system comprising a first chromatographic column and a pump for pumping a first mobile phase through the first chromatographic column; b) a second chromatographic analysis system comprising a second chromatographic column and a pump for pumping a second mobile phase through the second chromatographic column; c) means for selecting at least one compound-containing fraction from an effluent stream of the first chromatographic column and introducing the at least one compound-containing fraction into the second chromatographic column; wherein the pH of the first mobile phase and the pH of the second mobile phase are different.

Each of the first and second chromatographic analysis systems preferably includes an injector for introducing a sample or fraction into the system. Conventional multi-port rotary injection valves can be used. Pumps for liquid chromatographic systems are commercially available; a pump can be selected according to criteria such as the amount of solvent that must be pumped through the chromatographic system, and the back pressure present in the system. In certain embodiments, when gradient elution is used, it may be preferred to use multiple pumps in one or both of the first and second chromatographic systems.

The system of the invention can include a fraction collector for collecting eluent fractions from either or both of the first and second eluent streams. Thus, the means for selecting at least one compound-containing fraction from an effluent stream of the first chromatographic column include fraction collectors and the like, while the means for introducing the at least one compound-containing fraction into the second chromatographic column can include manual injectors or on-line injection systems (e.g., using a multi-port injection valve as a second-dimension injector) as described above. Alternatively, or additionally, the system can include a module for on-line dilution of portions or fractions of the first eluent stream.

The multi-dimensional HPLC system of the invention is preferably operated through a computerized control and data analysis system, preferably configured with software effective for operating the hardware of both chromatographic dimensions (sampling systems, injection valves, mobile-phase pumps, detection systems) and for effecting tracking and acquiring data from the hardware. Suitable software is commercially available, for example, from liquid chromatography systems manufacturers, such as Waters (Milford Mass.), and/or from software manufacturers, such as Lab View brand software. The software can additionally include control elements for operating robotic fluid handlers and other devices that may be integrated into the multi-dimensional HPLC system.

While the above description generally refers to systems and methods having first and second chromatographic separations systems, it will be apparent to the skilled artisan that additional chromatographic dimensions can be added, e.g., a third chromatographic separations system, e.g., to further improve separation of analytes not resolved by the first or second separations. For example, a third chromatographic dimension can be added. In preferred embodiments, an additional dimension is mutually orthogonal to one or more of the other dimensions. In preferred embodiments, an additional dimension is mutually orthogonal to one or all other utilized dimensions. Such multi-dimensional approaches may be especially useful, e.g., in separation and analysis of phosphopeptides, glycopeptides, highly acidic peptides, and the like.

EXAMPLES

Materials and Reagents

Trifluoroacetic acid (TFA), was purchased from Pierce (Rockford, Ill., USA). Formic acid (FA), concentrated ammonium hydroxide, ammonium formate, sodium hydrogen phosphate, phosphoric acid, and HPLC grade acetonitrile were purchased from J. T. Baker (Phillipsburg, N.J., USA). A Milli-Q system (Millipore, Bedford, Mass., USA) was used to prepare deionized water (18 MΩcm) for HPLC mobile phases. MassPREP peptide standard and MassPREP protein digest standards were obtained from Waters (Milford, Mass., USA).

2D-HPLC Experimental Setup

For LC-MS compatible HPLC modes such as RP, HILIC, and SEC, the MassPREP standards were directly injected on LC-MS system. The retention time of peptides (identified by their corresponding molecular weights) were plotted in graphs in order to compare the selectivity and orthogonality of different separation dimensions.

The SCX and HIC separation modes utilize high concentration of salts in the mobile phase. Therefore it was not possible to directly assign the retention times to eluting peptides (since their identity is unknown). Instead, fractions were collected in fine intervals (0.5-2 minutes) and later analyzed using either capillary LC-MS or MALDI MS.

HPLC Instrumentation

The reversed-phase (RP) chromatography, size exclusion chromatography (SEC) and hydrophilic-interaction chromatography (HILIC) experiments were carried out using a Model 2795 Alliance® HPLC system with a 2996 photodiode array detector and single quadrupole Micromass ZQ 4000 MS instrument (Waters, Milford, Mass., USA). MS conditions were as follows: capillary voltage was 3.2 kV, cone voltage 30V, extractor 1V, and RF lens 0.3 V. Source temperature was set to 100° C., desolvation to 350° C. Desolvation gas flow was set to 350 liters per hour, cone gas to 50 liters per hour. MS scan span was 300-2500 m/z, scan time 2.2 s with 0.1 s interscan time. Spectra were collected in positive ESI mode.

The strong cation exchange (SCX) chromatography and hydrophobic interaction (HIC) chromatography were carried out using a Model 2796 Alliance® MD HPLC system with a 2996 photodiode array detector. Fractions were collected manually.

Analysis of SCX and HIC Fractions: LC-MS and MALDI MS Instrumentation

Before LC-MS or MALDI MS analysis, collected fractions were desalted using an Oasis HLB 96-well microElution plate. The SCX or HIC fractions were diluted 1:1 with 0.2% aqueous TFA and loaded onto extraction plate (that was first conditioned with 200 µl of ACN followed by 200 µl of 0.1% TFA). After loading, the plate was washed with 200 µl of 0.1% TFA and the retained peptides were eluted with 60 µl of 60% acetonitrile (ACN) in water. About 1 µl of the eluent was mixed with MALDI matrix alpha-cyano-4-hydroxycinnamic acid (CHCA) and directly spotted on a stainless steel MALDI target for analysis. The matrix was prepared in 80% ACN at concentration 10 mg/ml, spiked with 100-500 fmole of a chosen peptide (ACTH) serving as an internal standard. Mass spectra were acquired by a Micromass M@LDI R TOF instrument (Waters, Milford Mass., USA) equipped with a pulsed $N_2$ laser (337 nm) and a 2.3 meter flight path and controlled by MassLynx 4.0 (Waters, Milford Mass., USA). This instrument was operated in reflectron mode with delayed extraction.

Fractions desalted and recovered from Oasis HLB plate were partially evaporated to reduce ACN content prior to LC-MS analysis. The final volume of each fraction was approximately 10 µl; 1 µl was injected on capillary RP-HPL column for analysis. A capillary HPLC system (CapLC™, Waters Corporation, Milford, Mass., USA) equipped with a photodiode array detector was connected to an ESI-Q-T of Micromass spectrometer (Micromass Q-Tof™ micro, Waters Corporation, Milford, Mass.) operated in MS mode. The capillary voltage was set to 3200 V, cone to 30 V, extraction cone to 0.5 V, ion energy 4 V, collision energy 10 V.

HPLC Experiments and Column Description

RP-HPLC, pH 2.6: A 2.1×150 mm, 3 µm Atlantis dC18 column (Waters Corporation, Milford, Mass., USA) was used with a flow rate of 200 µl/min; column temperature was set to 40° C. Mobile phase A was 0.2% formic acid (FA) in water, mobile phase B was 0.13% FA in ACN. Gradient was from 0 to 56% B in 70 minutes (0.8% ACN/minute).

RP-HPLC, pH 8.5 and 10: A 2.1×150 mm, 3.5 µm XTerra Phenyl (for pH 8.5) and 2.1×150 mm XTerra MS C18 columns (for pH 10) (Waters Corporation, Milford, Mass., USA) were used with a flow rate of 200 µl/min; column temperature was set to 40° C. Mobile phase A was 20 mM aqueous ammonium formate buffer, pH 8.5 or the same buffer pH 10; mobile phase B was ACN. Gradient was from 0 to 56% B in 70 minutes (0.8% ACN/minute).

RP-HPLC, pentafluorophenyl (PFP), 5 µm (Waters, Milford, Mass., USA): Mobile phase A was water, B acetonitrile, and C 400 mM $NH_4FA$ aqueous buffer; pH 3.25. Flow rate was 0.2 mL/minute, separation temperature 40° C. The gradient was 0.8% acetonitrile per minute; pump C was used to deliver isocratically 20% of solvent, so the mobile phase contained a constant concentration of 80 mM $NH_4FA$ buffer. The buffer was prepared by adding 24.7 g of concentrated ammonium hydroxide (28% aqueous solution) into 900 mL of water and 50 mL of FA (99%). The pH was adjusted either with ammonium hydroxide or FA to pH 3.25 and the volume was brought to 1 L.

HILIC: A 2.1×150 mm, 3 µm Atlantis HILIC column (Waters Corporation, Milford, Mass., USA) was used with a flow rate of 200 µl/min; column temperature was set to 40° C. Mobile phase A was water, mobile phase B was ACN and mobile phase C was aqueous 200 mM ammonium formate, pH 4.5. Gradient was from 90 to 40% B in 62.5 minutes (0.8% ACN/minute), the buffer C was kept constant at 5% (making the constant concentration 10 mM ammonium formate in mobile phase).

SEC: Three 4.6×250 mm, 5 µm YMC diol, 60 Å SEC columns (Waters Corporation, Milford, Mass., USA) were connected in series. Mobile phase was mixed using pumps: Mobile phase A was water, B acetonitrile, and C 200 mM ammonium formate ($NH_4FA$) aqueous buffer; pH 4.5. Flow rate was 0.2 mL/minute, separation temperature 40° C. The isocratic mobile phase contained 20% acetonitrile and 40 mM $NH_4FA$ buffer, pH 4.5. The buffer was prepared by dissolving 12.6 g of ammonium formate in 900 mL of water and adjusting pH to 4.5 with FA (99%); the volume was then brought to 1 L.

SCX-HPLC: A polySULFOETHYL Aspartamide™ SCX, 5 µm column (PolyLC, Columbia, Md., USA) was used for ion-exchange HPLC separations. The column was operated at 25° C. For certain experiments, the mobile phases were A: 20 mM $NaH_2PO_4$, pH 2.6 with 5% acetonitrile and B: 20 mM $NaH_2PO_4$, pH 3 with 5% in acetonitrile with addition of 1 M NaCl. Gradients was 0-15% B in 100 minutes. In other experiments, the conditions were as follows: the SCX experiment was carried out at 30° C. with flow rate 0.2 mL/min. Mobile phase A was water, B acetonitrile, and C 400 mM $NH_4FA$ aqueous buffer, pH 3.25. The gradient was from 10 to 75% C in 40 minutes; pump B was used to deliver isocratically 25% of acetonitrile for the entire duration of the salt gradient. The NH4FA buffer was compatible with direct MS detection.

Capillary LC-MS: The 0.3×150 mm, 3.5 µm bridged hybrid C18 column (Waters Corporation, Milford, Mass., USA) was used with a flow rate of 5 µl/min; column temperature was set to 40° C. Mobile phase A was 0.1% FA in water, mobile phase B was 0.1% FA in 80% ACN/20% water. Gradient was from 0 to 80% B in 64 minutes (1% ACN/minute).

Example 1

In this study we used tryptic digests of five proteins (250 peptides) for evaluation of orthogonality of various LC modes and development of alternative orthogonal LC separation approaches. The tested chromatographic modes (which were tested individually) included strong cation exchange (SCX), size exclusion (SEC), reversed-phase, (RP), and hydrophilic interaction (HILIC) chromatography. Retention of peptides was recorded for each separation, plotted into a 2D graph and mathematically correlated; the orthogonality of separation was evaluated as a fraction of area covered by eluting peaks in investigated 2D plots.

Figure 2:
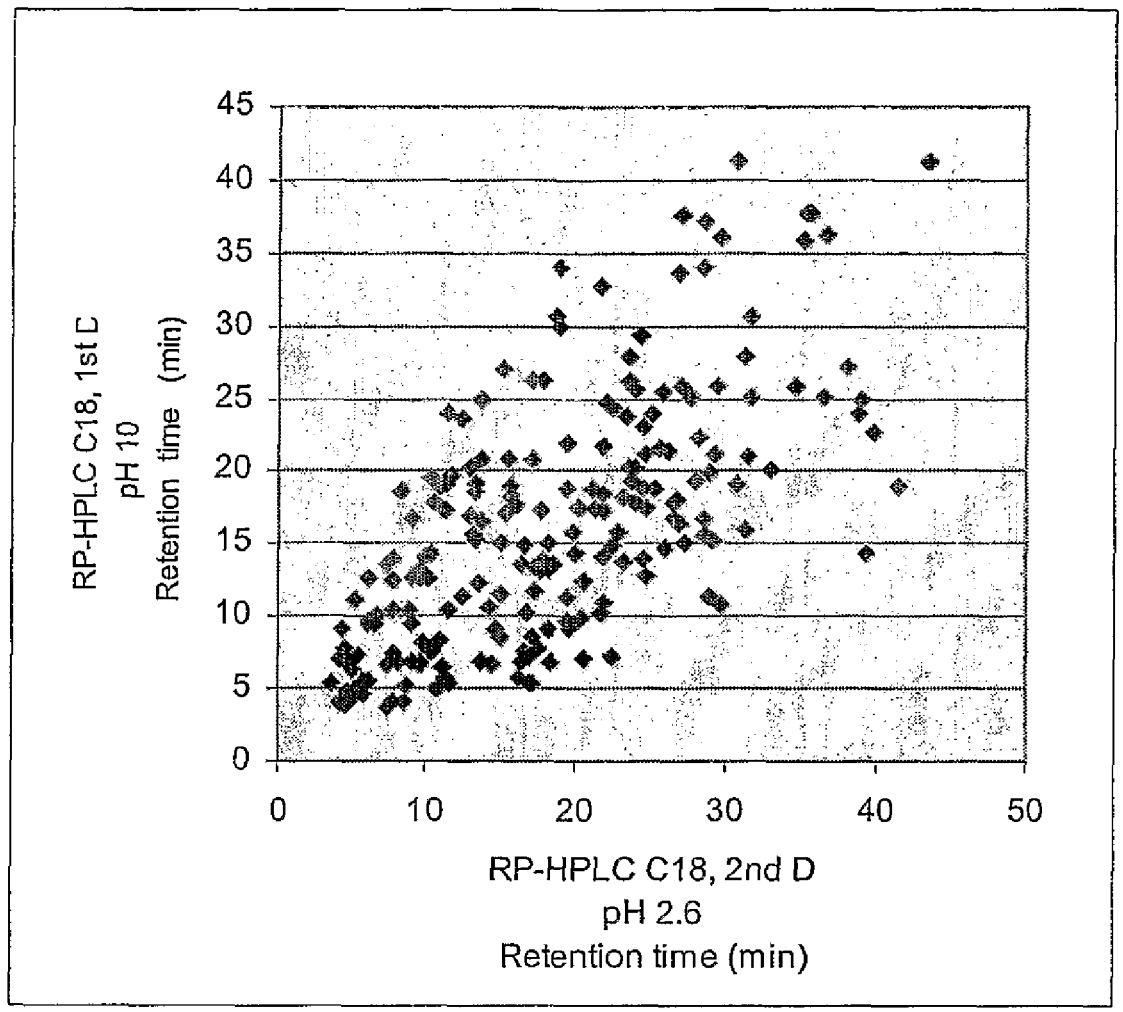
FIG. 2 is a plot showing the separation resulting from a multi-dimensional LC separation system using RP-HPLC in the first dimension and RP-HPLC in the second dimension.
Figure 3:
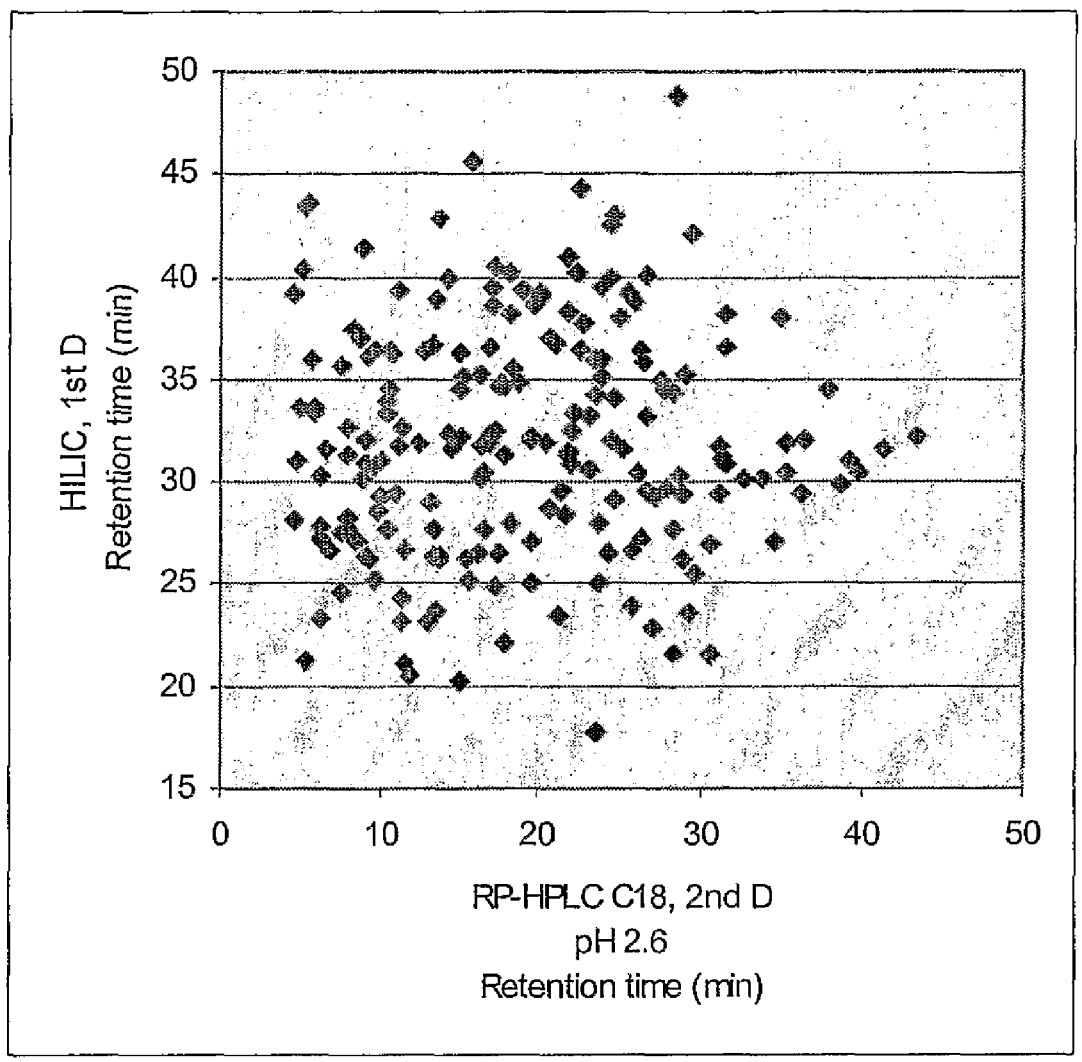
FIG. 3 is a plot showing the separation resulting from a multi-dimensional LC separation system using HILIC in the first dimension and RP-HPLC in the second dimension.

The results of these studies are shown in FIGS. 1-3. In FIG. 1, SCX separation (as described above) in one chromatographic dimension was compared to RP-HPLC on an Atlantis™ $C_{18}$ column. The key in FIG. 1 indicates the charge state of the peptide. In FIG. 2, RP-HPLC in one dimension (pH 2.6, Atlantis column, as described above) was compared to RP-HPLC on an Xterra MS C18 column at pH 10. In FIG. 3, HILIC separation in one dimension was compared to RP-HPLC on an Atlantis™ $C_{18}$ column at pH 2.6.

We found that the highest orthogonality among these conditions was obtained for the combination of HILIC with RP ($R^2=0.0038$) or for RP-RP ($R^2=0.45$). In the latter case the differential selectivity (which results in orthogonality) can be achieved by utilizing different mobile phases rather than varying a stationary phase. However, we have also found that RP-HPLC on an Atlantis C18 column at pH 2.6 is somewhat complementary to RP-HPLC on an Xterra Phenyl column at ph 8.5 ($R^2=0.78$, data not shown). In this case, the modest orthogonality may be due to the differing stationary phase as well as the pH difference. Other evaluated RP stationary phases show similar trends; the most distinct selectivity was observed for PFP sorbent (data not shown). However, the orthogonality is still limited and most of the 2D space is not used for separation.

Both HILIC and RP modes are highly efficient separation modes, suitable for analysis of peptides of broad range of hydrophobicity. In addition, the mobile phases used, including any additives, can be selected to be volatile, so the separation dimensions are interchangeable and are compatible with mass spectrometric analysis.

The SEC combined with RP also offers good orthogonality (results not shown), however, the low SEC peak capacity makes this separation dimension less attractive (at least for peptides). Because of the limited efficiency of SEC, we connected three columns in series to enhance the peak capacity and recorded the retention data. The residual interaction of relatively hydrophobic peptides with the sorbent was minimized by addition of 20% acetonitrile and 40 mM NH4FA buffer, pH 4.5 into a mobile phase. However, some secondary interaction still prevailed, limiting the recovery of larger peptides, and affecting the overall selectivity of separation. Only a loose correlation between size of the peptides and their SEC retention was observed. Longer peptides (more hydrophobic and therefore more retained in RP mode) elute earlier in SEC, as expected. However, the degree of orthogonality for RP×SEC combination is greater than one may expect (data not shown). This behavior is likely to be caused by the peptide secondary interaction with the sorbent, as mentioned above.

HILIC mode was also evaluated for peptide separation. Only a few reports have been published for peptide separation in HILIC mode, mostly using polyaspartate or amide sorbents. We have utilized a HILIC column packed with bare silica sorbent; both peptide peak shapes and recovery were good. No precipitation was observed when dissolving peptide samples in 70% acetonitrile prior to injection. Some correlation between peptide charge and their HILIC retention suggests that the retention mechanism includes both partitioning and ionic interaction (e.g., due to the charged silanols). Therefore, the separation selectivity partially resembles the peptide retention in SCX mode. The high degree of HILIC-RP system orthogonality makes it a promising approach for 2D-LC.

The combination of SCX-RP (FIG. 1) shows a lower degree of orthogonality compared to the RP-HPLC-RP-HPLC or RP-HPLC-HILIC examples above. The separation in SCX mode is primarily based on the peptide charge, hence the doubly and triply charged peptides tend to elute in clusters, leaving some other parts of separation less populated with peaks. Most of the tryptic peptides present in a typical sample are 2+ charged (60-80%); therefore the majority of components within a narrow range of retention times and are therefore not well resolved. In addition, under some conditions we observed loss of hydrophobic peptides in the SCX dimension despite the addition of 25% acetonitrile to a mobile phase (similar losses were seen for SEC as well). Approximately 30-40% peptides were not detected eluting from SCX in these instances. However, when SCX is used with a LC-MS compatible volatile mobile phase, all peptides of interest (including the hydrophobic ones) were detected (with both 25% or 5% of acetonitrile in mobile phase, data not shown). Without wishing to be bound by any theory, it appears that either the peptides are incompletely eluted from the SCX column (with NaCl eluent), in spite of the acetonitrile content in the mobile phase, or some post-collection precipitation occurs in the presence of a high concentration of non-volatile salts. We believe that LC-MS compatible buffers offer benefits for SCX fractionation of peptides.

These results show that combinations of certain separations can be used to obtain complementary separations which can be used for multi-dimensional separations. Differences in pH between the two separations can be used to provide substantial orthogonality even when the same separation mode (e.g., RP-HPLC) is used for both a first and a second separation dimension.

Example 2

SCX sorbents were investigated in greater detail. Elution in SCX mode is usually accomplished with a gradient of NaCl, which makes this mode incompatible with MS detection. Both off-line and on-line 2D-LC-MS setups usually rely on sample desalting, often realized via RP trapping columns. Previously published reports indicate that available SCX sorbents exhibit a secondary (hydrophobic) interaction, which reduces the recovery of hydrophobic peptides. It has been suggested that addition of organic solvents in a mobile phase improves the peak shape and peptide recovery. However, even with 25% acetonitrile in the mobile phases we observed lower number of peptides than expected. Therefore, we investigated alternative mobile phases and direct MS detection.

The mobile phase was prepared from volatile buffer, namely 400 mM ammonium hydroxide titrated to pH 3.25 with FA. The final concentration of FA was approximately 1.3 M (5% FA). Since the $pK_a$ of FA is 3.75, the pH of buffer (0.5 pH unit lower) insures that only 25% of FA is de-protonated, bringing the concentration of [H$^+$] to 325 mM. Together with the ammonium cation, the total cation strength of this buffer adds to 725 mM. The gradient from 10 to 75% of buffer (72.5 to 543.75 mM) successfully eluted all desirable peptides up to 5+ charge. The MS signal was not dramatically suppressed; on-line LC-MS detection was possible.

As expected, the SCX selectivity appears to be driven by peptide charge. Trends emerging from the plot suggest that peptide retention depends also on its length. The large peptides (that are more hydrophobic and better retained in RP) are relatively less retained in SCX chromatography compared to short peptides of the same charge. This behavior implies that charge density (which is greater for the shorter peptides) plays a secondary role in the retention mechanism. Without wishing to be bound by any particular theory, it is believed that the charge density is responsible for the ability of SCX sorbent to resolve peptides with the same charge rather than the residual hydrophobic interaction of the peptides with sorbent.

The orthogonality of SCX-RP combination appears to be good. However, in the plotted data, the most abundant groups of peptides (66% peptides are 2+ charged; 28% peptides are 3+ charged) form tight clusters. The 2D separation space is not covered with the data points uniformly, therefore the orthogonality is lower than anticipated.

Example 3

Additional experiments were performed to characterize RP-RP-HPLC as an approach to 2D-HPLC separation of peptides. An off-line 2D-HPLC experiment was set up to confirm the degree of achievable orthogonality. A sample comprising 5 digested proteins mixed in equimolar ratio (10 pmole each), was injected in a first RP-HPLC dimension at pH 10, using a 150×1 mm column packed with a novel 3.5 μm C18 bridged-ethyl hybrid (BEH) silica sorbent, recently developed for RP-HPLC applications (K. D. Wyndham et al., *Anal. Chem.* (2003), 75, 6781-6788). The BEH sorbent is highly stable at a broad range of pH, and provides an ideal material for separation at both pH 2.6 and 10.

Under these conditions, the average peak width is typically 0.5 minute at the baseline; 2.5 minute fractions (5 peak widths) were collected, and partially evaporated in order to reduce the acetonitrile and ammonium hydroxide content. The final volume of fractions was 10 μl; 1 μl was injected into a second LC-MS dimension using 150×0.3 mm, 3.5 μm BEH C18 capillary column.

The peptides eluting earlier in first LC dimension tend to elute earlier in the second dimension as well. Similarly, the peptides collected in later fractions elute later in second separation dimension. The orthogonality of separation appears to be good, especially when considering that the same type of C18 sorbent was used for first and second dimension, thus the orthogonality is generated solely via the pH effect. The gradient delay of the capillary LC system used was approximately 13 minutes; this specific time is not populated by the peaks. Few if any tryptic peptides elute beyond 43 minutes, making the useful separation window only 30 minutes wide. Most collected fractions eluting peptides cover 50-70% of the useful LC-MS time. Adjustment of the gradient starting strength and span for early, medium and later collected fractions can potentially spread the peptides over the separation space more evenly.

The orthogonality of RP—RP approach was compared to SCX-RP-HPLC system. A 150×2.1 mm SCX column was used with 4.4× greater peptide mass load of (in order to maintain the load proportional to RP-PR experiment with 1 mm i.d. column). Collected fractions were desalted by SPE and the final volume was reduced by evaporation to 44 μl. About 1 μl was analyzed by LC-MS; the mass load and separation conditions were identical to a previous RP—RP experiment. Under these conditions, the separation orthogonality was found to be comparable for both 2D-HPLC systems.

Example 4

The impact of pH on separation selectivity was first evaluated using an Enolase digest (approximately 35 peptides). The retention times acquired for mobile phase with pH 7.9 (10 mM ammonium bicarbonate), were plotted against the data recorded previously for mobile phase with FA, pH 2.6. The orthogonality of separation was noticeably greater than in some of the other experiments described herein. To clarify that the change in orthogonality is indeed due to the pH difference, we carried out another experiment. HPLC columns were packed with polar embedded RP-18 and Phenyl sorbent; separation was carried out using similar pH (7.9 and 8.5 respectively). No significant orthogonality was observed, in contrast to the orthogonality seen between pH 2.6 and pH 7.9, as described above.

The impact of pH was further investigated using a wider pH gap in both separation dimensions. The experimental data collected at pH 8.5 and 10 showed a significant degree of orthogonality when plotted against pH 2.6 retention data. Greater orthogonality was achieved for the wider pH difference between RP separation dimensions; therefore, further discussion focuses on the pH 2.6 versus pH 10 experiment. The separation at pH 10 was performed on hybrid-silica XTerra MS C18 stationary phase, known to be stable at elevated pH. The 20 mM ammonium formate buffer used for separation suppressed MS signal to a degree. However, all peptides masses were clearly detectable. Retention data at pH 10 were plotted against data from BioSuite C18 PA-A column using 0.2% FA in the mobile phases (pH 2.6). A relatively high spread of peptides over 2-D separation space was observed. The data were subdivided into three groups, according to the peptide pI values. A spatial separation emerging from the graph suggests that the main separation factor is indeed the pI (charge) of peptides. A class of acidic peptides (pI<5.5) is more strongly retained at pH 2.6, when the carboxylic moieties are not ionized, compared to basic peptides (pI>7.5) that are more strongly retained under pH 10 conditions (when they are, at least partially, discharged).

Some degree of orthogonality is observed also for the group of peptides within the 5.5-7.5 μl range. This observation deserves further comment. Peptides pI values represent the pH at which the molecule net charge is equal to zero. The pI is a sum of contributions of many ionizable amino acids, such as basic arginine (pKa 12.5), lysine (pKa 10.2), histidine (pKa 6.45), terminal amino group $NH_2$ (pKa 7.6), acidic amino acids such as aspartic acid (pKa 3.95), glutamic acid (pKa 4.45), tyrosine (pKa 9.8), and terminal COOH group (pKa 3.6). Even "neutral" peptides in pI range 5.5-7.5 should be affected by pH, since at least some of the ionizable groups will be differently charged/discharged at separation conditions (pH 2.6 or 10).

The contents of all patents and references cited herein are hereby incorporated by reference.

Other embodiments are included in this invention and the following claims, as will be appreciated by one of skill in the art in light of this disclosure.

What is claimed is:

1. A method for analyzing a sample containing at least one analyte, the method comprising:
   a) subjecting the sample to a first chromatographic separation mode at a first pH with a first mobile phase;
   b) collecting at least one fraction from the first chromatographic separation;
   c) subjecting the at least one fraction to a second chromatographic separation mode at a second pH with a second mobile phase; and
   d) detecting the presence or absence of the at least one analyte in the sample;
   wherein the first pH and the second pH differ by at least about 3 pH units.

2. The method of claim 1, wherein the first and second chromatographic separations are substantially orthogonal to each other.

3. The method of claim 1, wherein the first and/or second chromatographic separation mode is high performance liquid chromatography (HPLC).

4. The method of claim 1, wherein the first and/or second chromatographic separation mode is hydrophilic interaction chromatography (HILIC).

5. The method of claim 1 wherein an HPLC separation is a reversed-phase HPLC separation.

6. The method of claim 1 wherein the first chromatographic separation mode has a peak capacity of at least 100 peaks.

7. The method of claim 1, wherein the at least one analyte is a peptide, polypeptide, or protein.

8. The method of claim 1, wherein the at least one analyte is a small organic molecule.

9. The method of claim 1, wherein the sample contains at least 1000 analytes.

10. The method of claim 1, wherein the total peak capacity of the method is at least 1,000 peaks.

11. The method of claim 1, in which the HPLC separation is performed using a microbore column, capillary column, or nanocolumn.

12. The method of claim 1, wherein the at least one fraction collected in step b) is concentrated or diluted prior to subjecting the at least one fraction to the second chromatographic separation mode.

13. The method of claim 12, wherein the at least one fraction is concentrated by evaporation.

14. The method of claim 12, wherein the at least one fraction collected in step b) is diluted on-line prior to performing the second chromatographic separation mode.

15. The method of claim 1, wherein the step of detecting is performed using mass spectrometry.

16. The method of claim 1, wherein the first and second chromatographic modes are the same.

17. The method of claim 1, wherein the first and/or second mobile phase is substantially free of non-volatile salts.

18. The method of claim 1, wherein the first and/or second mobile phase comprises less than about 20 mM of non-volatile salts.

19. The method of claim 1, wherein a plurality of portions are collected and subjected to the second chromatographic separation.

20. The method of claim 1, wherein the first and second chromatographic separation modes comprise liquid chromatographic separations.

21. A method for separating a plurality of analytes in a sample, the method comprising:
   a) subjecting at least a portion of the sample to a first chromatographic separation mode at a first pH;
   b) collecting at least one fraction from the first chromatographic separation; and
   c) subjecting the at least one fraction to a second chromatographic separation mode at a second pH, wherein the first pH and the second pH differ by at least about 3 pH units; under conditions such that at least two analytes in the sample are separated.

22. The method of claim 21, wherein the first and second chromatographic separation modes comprise HPLC separations.

23. The method of claim 21, wherein the first and second chromatographic separations are substantially orthogonal to each other.

24. The method of claim 21, wherein the first and/or second chromatographic separation mode is high performance liquid chromatography (HPLC).

25. The method of claim 21, wherein the first and/or second chromatographic separation mode is hydrophilic interaction chromatography (HILIC).

26. The method of claim 21 wherein an HPLC separation is a reversed-phase HPLC separation.

27. The method of claim 21 wherein the first chromatographic separation mode has a peak capacity of at least 100 peaks.

28. The method of claim 21, wherein the at least one analyte is a peptide, polypeptide, or protein.

29. The method of claim 21, wherein the at least one analyte is a small organic molecule.

30. The method of claim 21, wherein the sample contains at least 1000 analytes.

31. The method of claim 21, wherein the total peak capacity of the method is at least 10,000 peaks.

32. The method of claim 21, in which the HPLC separation is performed using a microbore column, capillary column, or nanocolumn.

33. The method of claim 21, wherein the at least one fraction collected in step b) is concentrated or diluted prior to subjecting the at least one fraction to the second chromatographic separation mode.

34. The method of claim 21, wherein the step of detecting is performed using mass spectrometry.

35. The method of claim 21, wherein the first and second chromatographic modes are the same.

36. The method of claim 21, wherein the first and/or second mobile phase is substantially free of non-volatile salts.

37. The method of claim 21, wherein the first and/or second mobile phase comprises less than about 20 mM of non-volatile salts.

38. The method of claim 21, wherein a plurality of portions are collected and subjected to the second chromatographic separation.

39. A method for characterizing a sample containing a plurality of polypeptides in a multi-dimensional liquid chromatography system, the method comprising:
   a) injecting the sample into a first dimension chromatography apparatus of said multi-dimensional liquid chromatography system;
   b) chromatographically separating at least a first polypeptide component of said sample from at least a second polypeptide of said sample in a chromatography column of said first dimension chromatography apparatus using a first mobile phase;
   c) eluting said separated first and second polypeptide components in an eluent from said chromatography column;
   d) sampling at least one discrete volume of said eluent;

e) injecting said at least one discrete volume into a second dimension chromatography apparatus of said multi-dimensional liquid chromatography system;

f) subjecting the injected discrete volume to a chromatographic separation in a chromatography column of said second dimension chromatography apparatus using a second mobile phase, wherein the pH of said first and second mobile phases differs by about 3 pH units;

g) characterizing an eluent from said chromatography column of said second dimension chromatography apparatus using mass spectroscopy, thereby characterizing the sample containing a plurality of polypeptides.

40. The method of claim 39, wherein the multi-dimensional liquid chromatography system comprises a two-dimensional liquid chromatography system.

41. A method for purifying a compound in a sample containing the compound and at least two impurities, the method comprising:

a) subjecting the sample to a first chromatographic separation mode at a first pH, under conditions such that the compound is separated from a first impurity;

b) collecting at least one compound-containing fraction from the first chromatographic separation;

c) subjecting the at least one compound-containing fraction to a second chromatographic separation mode at a second pH, under conditions such that the compound is separated from a second impurity, wherein the first pH and the second pH differ by at least about 3 pH units; and d) collecting the purified compound.

42. A method for analyzing a sample containing at least one analyte, the method comprising:

a) subjecting the sample to a first chromatographic separation at a first pH with a first mobile phase;

b) collecting at least one portion from the first chromatographic separation;

c) subjecting the at least one portion to a second chromatographic separation at a second pH with a second mobile phase, wherein the first pH and the second pH differ by at least about 3 pH units; and d) detecting the presence or absence of the at least one analyte in the sample;

wherein both the first and second mobiles phases are substantially free of non-volatile salts.

* * * * *